US006336454B1

(12) United States Patent
Farrell et al.

(10) Patent No.: US 6,336,454 B1
(45) Date of Patent: Jan. 8, 2002

(54) NASAL VENTILATION AS A TREATMENT FOR STROKE

(75) Inventors: Peter Craig Farrell, LaJolla, CA (US); Gary William Pace, Winchester, MA (US)

(73) Assignee: ResMed Limited, North Ryde (AU)

( * ) Notice: Subject to any disclaimer, the term of this patent is extended or adjusted under 35 U.S.C. 154(b) by 0 days.

(21) Appl. No.: 09/079,848

(22) Filed: May 15, 1998

Related U.S. Application Data

(60) Provisional application No. 60/046,746, filed on May 16, 1997.

(51) Int. Cl.$^7$ .................. A61M 15/00; A61M 16/00; A62B 18/00; A62B 7/00; A62B 9/00
(52) U.S. Cl. .................................. 128/200.24
(58) Field of Search .................. 128/202.12, 204.18, 128/204.21, 204.25, 200.24

(56) References Cited

U.S. PATENT DOCUMENTS

| | | | |
|---|---|---|---|
| 1,224,180 A | * 5/1917 | Lake | ..... 128/202.12 |
| 2,712,927 A | 7/1955 | Blum | |
| 2,953,355 A | 9/1960 | Hungate | |
| 3,099,985 A | 8/1963 | Wilson et al. | |
| 3,502,100 A | 3/1970 | Jonson | |
| 3,659,604 A | 5/1972 | Melville et al. | |
| 3,726,270 A | 4/1973 | Griffis et al. | |
| 3,741,208 A | 6/1973 | Jonsson et al. | |
| 3,783,893 A | 1/1974 | Davison | |
| 3,869,529 A | 3/1975 | Follette | |
| 3,903,875 A | 9/1975 | Hughes | |
| 3,903,883 A | 9/1975 | Pecina et al. | |
| 3,914,994 A | 10/1975 | Banner | |
| 3,932,054 A | 1/1976 | McKelvey | |
| 3,985,467 A | 10/1976 | Lefferson | |
| 3,987,133 A | 10/1976 | Andra | |
| 3,992,598 A | 11/1976 | Welsh et al. | |
| 3,995,661 A | 12/1976 | Van Fossen | |
| 4,051,205 A | 9/1977 | Grant | |
| 4,060,576 A | 11/1977 | Grant | |
| 4,109,749 A | 8/1978 | Sweet | |
| 4,110,419 A | 8/1978 | Miller | |
| 4,119,096 A | 10/1978 | Drews | |
| 4,201,204 A | 5/1980 | Rinne et al. | |
| 4,203,027 A | 5/1980 | O'Hare et al. | |
| 4,206,754 A | 6/1980 | Cox et al. | |
| 4,249,527 A | 2/1981 | Ko et at. | |
| 4,301,833 A | 11/1981 | Donald, III | |

(List continued on next page.)

FOREIGN PATENT DOCUMENTS

| | | | |
|---|---|---|---|
| AU | A-62221/90 | * | 3/1991 |
| AU | A-33877/93 | * | 4/1993 |
| AU | B-59270/90 | * | 5/1993 |
| AU | A-38508/93 | * | 7/1993 |
| AU | A-48748/93 | * | 9/1993 |
| AU | A-52628/93 | | 7/1994 |
| AU | B 79174/94 | | 6/1995 |
| AU | 9226120 | | 7/1995 |
| AU | A-34471/95 | * | 2/1996 |
| AU | A-40711/95 | * | 4/1996 |
| AU | B 34354/95 | | 5/1996 |
| AU | A 39130/95 | | 6/1996 |
| DE | 459104 | | 4/1928 |

(List continued on next page.)

OTHER PUBLICATIONS

Nachtman et al., Cheyne–Stokes respiration in ischemic stroke, Neurology 45:820–821, Apr. 1995.*

Bassetti et al., Sleep apnea in patients with transient ischemic attack and stroke: Aprospective study of 59 patients, Neurology 47:1167–1173, Nov. 1996.*

Krachman et al., Comparison of oxygen therapy with nasal CPAP on Cheyne–Stokes respiration during sleep in congestive heart failure, Chest V. 116, I 6 pp. 1550–1565, Dec. 1999.*

Dyken et al., Investigating the relationshp between Stroke and Obstructive Sleep Apnea, Stroke vol. 27: No. 3, pp. 401–407, Mar. 1996.*

Good et al., Stroke and Sleep Apnea, Neurology Network Commentary, 1:269–275, Dec. 1997.*

Good et al., Sleep–Disordered breathing and Poor functional outcome after stroke, Stroke vol. 27, No. 2, pp. 252–259, Feb. 1996.*

Puritan/Bennett Companion 320 I/E Bi–level Respiratory System Clinical Manual (for part No. 799959 Rev. A), Jan. 26, 1996.*

New! Breas PV 100 CPAP First Class Quality and Function. At the right Price; Jul. 4, 1998, pp. 1–2.

PV 101 Bi Level CPAP and PV 102 Bi–Level Time; pp 1–3, Dec. 10, 1998.

Prodigy Medical Supplies Co. Ltd.; CPAP.

Puritan Bennett; Companion 318 Nasal CPAP System; 5/93.

Nellcor Puritan Bennett; Announcing the Goodnight 314 and GoodKnight 318 Nasal CPAP Systems, 1996.

Puritan Bennett; Clean, Quiet, and Comfortable . . . The Companion's 515 Nasal CPAP System; 6/88.

DeVilbiss Night Guard Nasal CPAP for the Tretment of Obstructive Sleep Apnea.

Sunrise; DeVilbiss Horizon LT 8001 Nasal CPAP Therapy Small in Size, big on features; 8/97.

(List continued on next page.)

Primary Examiner—John G. Weiss
Assistant Examiner—Joseph F. Weiss, Jr.
(74) Attorney, Agent, or Firm—Pillsbury Winthrop LLP

(57) ABSTRACT

A new treatment and apparatus for acute and chronic treatment is described here which incorporates nasal ventilation, with or without concomitant drug therapy, using continuous positive airway pressure (CPAP) or bi-level pressure treatment or variants thereof, including devices which automatically set their pressures based on physiologic data inputs.

4 Claims, No Drawings

U.S. PATENT DOCUMENTS

| | | |
|---|---|---|
| 4,312,235 A | 1/1982 | Daigle |
| 4,346,048 A | 8/1982 | Gates |
| 4,387,722 A | 6/1983 | Kearns |
| 4,389,353 A | 6/1983 | Gates |
| 4,396,034 A | 8/1983 | Cherniak |
| 4,448,035 A | 5/1984 | Moriyama et al. |
| 4,448,058 A | 5/1984 | Jaffe et al. |
| 4,449,525 A | 5/1984 | White et al. |
| 4,481,944 A | 11/1984 | Bunnell |
| 4,499,914 A | 2/1985 | Schebler |
| 4,519,399 A | 5/1985 | Hori |
| 4,530,334 A | 7/1985 | Pagdin |
| 4,558,710 A | 12/1985 | Eichler |
| 4,579,114 A | 4/1986 | Gray et al. |
| 4,590,772 A | 5/1986 | Nose et al. |
| 4,592,349 A * | 6/1986 | Bird ................... 128/204.25 |
| 4,592,880 A | 6/1986 | Murakami |
| 4,595,139 A | 6/1986 | Levine |
| 4,621,632 A | 11/1986 | Bartels et al. |
| 4,655,213 A | 4/1987 | Rapoport et al. |
| 4,677,975 A | 7/1987 | Edgar et al. |
| 4,686,974 A | 8/1987 | Sato et al. |
| 4,747,403 A | 5/1988 | Gluck et al. |
| 4,773,411 A | 9/1988 | Downs |
| 4,795,314 A | 1/1989 | Prybella et al. |
| 4,802,485 A | 2/1989 | Bowers et al. |
| 4,819,629 A | 4/1989 | Jonson |
| 4,827,922 A | 5/1989 | Champain et al. |
| 4,838,258 A | 6/1989 | Dryden et al. |
| 4,856,506 A | 8/1989 | Jinotti |
| 4,870,960 A | 10/1989 | Hradek |
| 4,870,963 A | 10/1989 | Carter |
| 4,913,401 A | 4/1990 | Handke |
| 4,928,684 A | 5/1990 | Breitenfelder et al. |
| 4,938,210 A | 7/1990 | Shene |
| 4,938,212 A | 7/1990 | Snook et al. |
| 4,944,310 A | 7/1990 | Sullivan |
| 4,957,107 A | 9/1990 | Sipin |
| 4,986,269 A | 1/1991 | Hakkinen |
| 4,989,599 A | 2/1991 | Carter |
| 5,007,420 A * | 4/1991 | Bird ................... 128/200.14 |
| 5,009,635 A | 4/1991 | Scarberry |
| 5,024,219 A | 6/1991 | Dietz |
| 5,046,491 A | 9/1991 | Derrick |
| 5,048,515 A | 9/1991 | Sanso |
| 5,063,922 A | 11/1991 | Hakkinen |
| 5,063,938 A | 11/1991 | Beck et al. |
| 5,065,756 A | 11/1991 | Rapoport |
| 5,099,837 A | 3/1992 | Russel, Sr. et al. |
| 5,105,354 A | 4/1992 | Nishimura |
| 5,107,830 A | 4/1992 | Younes |
| 5,107,831 A | 4/1992 | Halpern et al. |
| 5,116,088 A * | 5/1992 | Bird ....................... 285/319 |
| 5,117,819 A | 6/1992 | Servidio et al. |
| 5,129,390 A | 7/1992 | Chopin et al. |
| 5,134,995 A | 8/1992 | Gruenke et al. |
| 5,148,802 A | 9/1992 | Sanders et al. |
| 5,161,525 A | 11/1992 | Kimm et al. |
| 5,163,423 A | 11/1992 | Suzuki |
| 5,165,398 A | 11/1992 | Bird |
| 5,178,138 A | 1/1993 | Walstrom et al. |
| 5,183,983 A | 2/1993 | Knop |
| 5,199,424 A | 4/1993 | Sullivan et al. |
| 5,203,343 A | 4/1993 | Axe et al. |
| 5,230,330 A | 7/1993 | Price |
| 5,231,979 A | 8/1993 | Rose et al. |
| 5,231,983 A | 8/1993 | Matson et al. |
| 5,239,994 A | 8/1993 | Atkins |
| 5,239,995 A | 8/1993 | Estes et al. |
| 5,240,177 A | 8/1993 | Muramatsu et al. |
| 5,245,995 A | 9/1993 | Sullivan et al. |
| 5,259,373 A | 11/1993 | Gruenke et al. |
| 5,271,391 A | 12/1993 | Graves |
| 5,280,784 A | 1/1994 | Kohler |
| 5,293,864 A | 3/1994 | McFadden |
| 5,303,698 A | 4/1994 | Tobia et al. |
| 5,303,700 A | 4/1994 | Weismann et al. |
| 5,305,787 A | 4/1994 | Thygesen |
| 5,311,875 A | 5/1994 | Stasz |
| 5,313,937 A | 5/1994 | Zdrojkowski |
| 5,322,057 A | 6/1994 | Raabe et al. |
| 5,335,654 A | 8/1994 | Rapoport |
| 5,335,656 A | 8/1994 | Bowe et al. |
| 5,343,878 A | 9/1994 | Scarberry et al. |
| 5,353,788 A | 10/1994 | Miles |
| 5,367,604 A | 11/1994 | Murray |
| 5,373,842 A | 12/1994 | Olsson et al. |
| 5,388,571 A | 2/1995 | Roberts et al. |
| 5,398,673 A | 3/1995 | Lambert |
| 5,400,777 A | 3/1995 | Olsson et al. |
| 5,404,871 A | 4/1995 | Goodman et al. |
| 5,433,193 A | 7/1995 | Sanders et al. |
| 5,443,061 A | 8/1995 | Champain et al. |
| 5,458,137 A | 10/1995 | Axe et al. |
| 5,479,920 A | 1/1996 | Piper et al. |
| 5,490,502 A | 2/1996 | Rapoport et al. |
| 5,492,113 A | 2/1996 | Estes et al. |
| 5,503,148 A | 4/1996 | Froehlich et al. |
| 5,509,404 A | 4/1996 | Lloyd et al. |
| 5,509,414 A | 4/1996 | Hok |
| 5,517,983 A | 5/1996 | Deighan et al. |
| 5,522,382 A | 6/1996 | Sullivan et al. |
| 5,526,805 A | 6/1996 | Lutz et al. |
| RE35,295 E | 7/1996 | Estes et al. |
| 5,535,739 A | 7/1996 | Rapoport et al. |
| 5,537,997 A | 7/1996 | Mechlenburg et al. |
| 5,540,219 A | 7/1996 | Mechlenburg et al. |
| 5,540,220 A | 7/1996 | Gropper |
| 5,635,738 A | 7/1996 | Estes et al. |
| 5,546,933 A | 8/1996 | Rapoport et al. |
| 5,551,418 A | 9/1996 | Estes et al. |
| 5,551,419 A | 9/1996 | Froehlich et al. |
| 5,558,084 A | 9/1996 | Daniell et al. |
| RE35,339 E | 10/1996 | Rapoport |
| 5,564,415 A | 10/1996 | Dobson et al. |
| 5,567,127 A | 10/1996 | Wentz |
| 5,570,682 A | 11/1996 | Johnson |
| 5,590,644 A | 1/1997 | Rosenkoetter |
| 5,590,648 A * | 1/1997 | Mitchell et al. ............ 128/630 |
| 5,598,837 A | 2/1997 | Sirianne, Jr. et al. |
| 5,598,838 A | 2/1997 | Servidio et al. |
| 5,608,647 A | 3/1997 | Rubsamen et al. |
| 5,617,846 A | 4/1997 | Graetz et al. |
| 5,632,269 A | 5/1997 | Zdrojkowski |
| 5,633,552 A | 5/1997 | Lee et al. |
| 5,642,730 A | 7/1997 | Baran |
| 5,645,053 A | 7/1997 | Remmers et al. |
| 5,645,054 A | 7/1997 | Cotner et al. |
| 5,655,520 A | 8/1997 | Howe et al. |
| 5,655,522 A | 8/1997 | Mechlenburg et al. |
| 5,666,946 A | 9/1997 | Langenback |
| 5,673,687 A | 10/1997 | Dobson et al. |
| 5,682,878 A | 11/1997 | Ogden |
| 5,685,293 A * | 11/1997 | Watt ..................... 128/202.12 |
| 5,685,296 A | 11/1997 | Zdrojkowski et al. |
| 5,701,883 A | 12/1997 | Hete et al. |
| 5,704,345 A | 1/1998 | Berthon-Jones |
| 5,715,812 A | 2/1998 | Deighan et al. |
| 5,730,121 A | 3/1998 | Hawkins et al. |
| 5,740,795 A | 4/1998 | Brydon |
| 5,794,615 A * | 8/1998 | Estes ..................... 128/204.23 |

| | | | |
|---|---|---|---|
| 5,823,187 A | 10/1998 | Estes et al. | |
| 5,862,802 A * | 1/1999 | Bird | 128/204.18 |
| 5,901,704 A * | 5/1999 | Estes et al. | 128/204.23 |
| 5,904,141 A * | 5/1999 | Estes et al. | 128/204.23 |
| 6,041,780 A * | 3/2000 | Richard et al. | 128/204.18 |
| 6,015,575 A * | 8/2000 | Estes et al. | 128/204.23 |

FOREIGN PATENT DOCUMENTS

| | | |
|---|---|---|
| DE | 3015279 A1 | 10/1981 |
| DE | 34 02 603 A1 | 8/1985 |
| DE | 3537507 A1 | 4/1987 |
| DE | 3539073 A1 | 5/1987 |
| DE | 4432219 C1 * | 4/1996 |
| EP | 0 062 166 A2 | 10/1982 |
| EP | 0 666 451 A1 | 12/1982 |
| EP | 0 088 761 B1 | 9/1983 |
| EP | 0 164 500 A2 | 3/1985 |
| EP | 0 171 321 A1 | 2/1986 |
| EP | 0 185 980 | 7/1986 |
| EP | 0 236 850 A2 | 9/1987 |
| EP | 0 872 643 A2 | 3/1988 |
| EP | 298 367 A2 | 1/1989 |
| EP | 0 388 525 A1 | 9/1990 |
| EP | 0 425 092 A1 * | 5/1991 |
| EP | 481 459 A1 | 4/1992 |
| EP | 0549299 A2 * | 6/1993 |
| EP | 0 535 952 A1 | 7/1993 |
| EP | 606 687 A2 | 7/1994 |
| EP | 0705615 A1 * | 9/1994 |
| EP | 0 714 670 A2 * | 12/1994 |
| EP | 0 656 216 A2 * | 6/1995 |
| EP | 0 661 071 A1 * | 7/1995 |
| EP | 178 925 A2 | 4/1996 |
| EP | 0 709 107 A1 * | 5/1996 |
| EP | 0 788 805 A2 * | 8/1997 |
| EP | 0 839 545 A1 | 5/1998 |
| EP | 0 845 277 | 6/1998 |
| FR | 2 574 657 A1 | 6/1986 |
| FR | 2 630 917 | 11/1989 |
| FR | 2 672 221 | 8/1992 |
| FR | 2682042 A1 | 4/1993 |
| GB | 1 294 808 | 11/1972 |
| GB | 1432572 | 4/1976 |
| GB | 1 444 053 | 7/1976 |
| GB | 2 077 444 A | 12/1981 |
| GB | 2 147 506 A | 5/1985 |
| GB | 2 164 569 A | 3/1986 |
| GB | 2 205 167 A | 11/1988 |
| GB | 2 254 700 A | 10/1992 |
| GB | 2 271 811 A | 4/1994 |
| GB | 2 284 400 A * | 5/1996 |
| JP | 54-104369 | 8/1979 |
| JP | 60-212607 | 10/1985 |
| JP | 62-103297 | 4/1987 |
| JP | 63-275352 | 11/1988 |
| JP | 2-173397 | 12/1988 |
| JP | 4-70516 | 3/1992 |
| JP | 4-70516 A | 3/1992 |
| JP | 06249741 A * | 9/1994 |
| JP | 6-249742 A * | 9/1994 |
| JP | 07280609 A | 10/1995 |
| JP | 8019610 A * | 1/1996 |
| SE | 1710064 A1 | 2/1992 |
| SE | 467041 B | 5/1992 |
| WO | WO 80/01044 | 5/1980 |
| WO | WO 82/03326 | 10/1982 |
| WO | WO 82/03548 | 10/1982 |
| WO | WO 86/05965 | 10/1986 |
| WO | WO 86/06969 | 12/1986 |
| WO | WO 88/10108 | 12/1988 |
| WO | WO 90/14121 * | 11/1990 |
| WO | WO 92/11054 * | 7/1992 |
| WO | WO 92/15353 | 9/1992 |
| WO | WO 92/22244 * | 12/1992 |
| WO | WO 93/08857 | 5/1993 |
| WO | WO 93/09834 | 5/1993 |
| WO | WO 93/21982 | 11/1993 |
| WO | WO 93/24169 * | 12/1993 |
| WO | WO 94/16759 | 8/1994 |
| WO | WO 94/20051 | 9/1994 |
| WO | WO 94/23780 * | 10/1994 |
| WO | WO 95/32016 * | 11/1995 |
| WO | WO 96/16688 | 6/1996 |
| WO | WO 96/35911 | 11/1996 |
| WO | WO 96/40337 * | 12/1996 |
| WO | WO 97/02064 * | 1/1997 |
| WO | WO 97/10019 * | 3/1997 |
| WO | WO 97/10868 * | 3/1997 |
| WO | WO 97/15343 * | 5/1997 |
| WO | WO 97/28838 | 8/1997 |
| WO | WO 97/41812 | 11/1997 |
| WO | WO 98/04311 | 2/1998 |
| WO | WO 98/06449 | 2/1998 |
| WO | WO 98/25662 | 6/1998 |
| WO | WO 98/33433 | 8/1998 |
| WO | WO 98/35715 | 8/1998 |
| WO | WO 98/36245 | 8/1998 |
| WO | WO 98/36338 | 8/1998 |
| WO | WO 98/47554 | 10/1998 |
| WO | WO 98/57691 | 12/1998 |

OTHER PUBLICATIONS

Devilbiss; Revitalizer Soft Start; The Facts Speak for Themselves, 1992.
Tranquility; Performance CPAP Advantage.
Healthdyne International; Tranquility Plus.
Respironics Inc.; Respironics' Solo CPAP System Provides Simplified OSA Therapy at an Outstanding value; Sep. 19, 1996.
Respironics Inc.; The First Family of OSA Therapy; 1991.
Fisher & Paykel Healthcare; HC200 Series Nasal CPAP Blower & Heated Humidifier.
Pierre Medical; Morphee Plus appareil de traitment des apnees due sommeil manuel d'utilisation.
Weinmann:Hamburg; Somnotron nCPAP–Gerat WM 23000, 11/91.
Puritan Bennent; 515a Part of Our Blueprint for the Future; 03/90.
Puritan Bennett; Companion 320 I/E Bi–Level Respiratory System; 4/93.
ResMed; Sullivan VPAP II & II ST.
Resmed; The Sullivan V Family of CPAP Systems; 1996.
Resmed; The AutoSet Portable II; 1997.
ResMed; Sullivan Nasal CPAP System.
ResMed; The Sullivan IIID; 1995.
ResMed; The Sullivan Comfort; 1996.
DeVilbiss a Division of Sunrise Medical; Expand your Horizons With The Horizons; 1995.
Healthdyne Technologies; Home Health Care Dealer; The Journal of Home Medical Equipment and Services/Supplier; Nov. and Dec. 1997.
Healthdyne International; Tranquility Quest, The Compact CPAP for Greater patient comfort.
AirStep; Medical Products . . . Stand the Test of Time.
MAP Medical Progress for Physician und Patient; The Gentle Therapy for Sleep–Related Breathing Disorders.
Taema; Ventilation CP 90, 5/95.
DPAP; Breath, by breath, by breath.

Lifecare; Smallest. Quietest. Smartest.
Lifecare; Quiet CPAP System for Maximum Compliance; 1991.
Lifecare; Software Nasal Mask, Custom Nasal Masks; 1991.
Nidek Medical; Silenzio.
Weinmann; Just to Feel Well, Sensitive Sleep Apnea Therapy with Somnotron 3 and Somno–Mask System.
Respironics Inc.; Aria CPAP System; 1993.
Respironics Inc.; SleepEasy III A New Dawn in Patient Compliance.
Respironics Inc.; Multiple Choice REMstar Choice Nasal CPAP System, 1993.
MaxII nCPAP and Moritz II Bi–Level Brochure.

Derwent: Flowmeter for fluids–has turbine transducer and volumetric sensor for simultaneous calibration, 1995.

Mark Kantrowitz, Erik Horskotte and Cliff Joslyn; "Answers to Frequently Asked Questions about Fuzzy Logic and Fuzzy Expert Systems" Version 1.24 last Modified Feb. 20, 1996.

Pressman et al., "Transient Ischemic Attacks and Minor Stroke During Sleep—Relationship to Obstruction Sleep Apnea Syndrome," pp. 2361–2365, Dec., 1995, Stroke vol. 26 No. 12.

* cited by examiner

NASAL VENTILATION AS A TREATMENT FOR STROKE

This application claims priority under 35 U.S.C. §119(e) to prior U.S. Provisional Patent Application Serial No. 60/046,746 entitled "NASAL VENTILATION AS A TREATMENT FOR STROKE", filed on May 16, 1997, the disclosure of which is hereby incorporated by reference in its entirety.

FIELD OF THE INVENTION

The present invention relates to a method of treatment and apparatus for stroke patients.

BACKGROUND OF THE INVENTION

Stroke, or brain attack as it is commonly called, can be caused by either vascular hemorrhage or vascular blockage with the latter accounting for about 80% of the events which lead to a stroke. Stroke is associated with considerable morbidity in terms of long-term neurological deficit and the risk of subsequent stroke as well as mortality post stroke is considerable in stroke patients. Treatment in the acute phase typically entails the invasive administration of clot dissolving drugs within the first three hours of the stroke as well as stabilization of cardiovascular function and vital signs. Post stroke therapy can include intensive and costly rehabilitation depending on the degree of neurological deficit.

Continuous positive airway pressure (hereinafter CPAP) has been identified as a method of treatment for sleep disorders, and in particular, sleep apnea. The application of CPAP for sleep disorders was first introduced in U.S. Pat. No. 4,944,310. This patent described the application of continuous positive airway pressure being applied to the patient, through the patient's nares, to treat sleep disorders, including obstructive sleep apnea. It has been found that the application of pressure which exceeds atmospheric pressure, typically 4 to 15 centimeters of $H_2O$ is useful in treating sleep disorders. However, prior to this invention, the application of CPAP as a method for treating stroke patients has never been known.

There exists a need for a method of treatment for stroke patients which is non-invasive, and does not include the use of drugs.

There also exists a need for the treatment of stroke patients which is inexpensive and does not require a medical facility or hospital.

SUMMARY OF THE INVENTION

A new treatment and apparatus for acute and chronic treatment of stroke patients is described here which incorporates nasal ventilation, with or without concomitant drug therapy, using continuous positive airway pressure (CPAP) or bi-level pressure treatment or variants thereof, including devices which automatically set their pressures based on physiologic data inputs.

DETAILED DESCRIPTION OF THE PREFERRED EMBODIMENT

Nasal CPAP treatment has been traditionally used for the management of patients with obstructive sleep apnea where CPAP acts as a pneumatic splint to maintain upper airway patency and therefore ensures free flow of air while the patient sleeps. The current invention describes the use of positive pressure ventilation, which may include CPAP, bi-level pressure, or variants thereof, for stroke patients. The use of CPAP treats stroke patients by improving arterial blood oxygen levels and reducing arterial carbon dioxide levels as well as improving auto-regulation of, for example, blood pressure, cardiac output and ventilation. Improvements in morbidity, such as rate and degree of recovery of vital signs and patient stabilization in the acute phase, is an expected benefit.

Also, an improvement in neurological deficits in the short and/or long term is an expected benefit.

An apparatus for the treatment of stroke patients is also disclosed herein. The apparatus comprises an airflow generator; an interface adapted to fit a patient; and a conduit for the flow of air from the generator to the interface. In one embodiment, the airflow being delivered to the interface is at a pressure which exceeds atmospheric pressure for at least a portion of a breathing cycle of the patient.

It is understood that while the invention has been described above in conjunction with the preferred method and preferred embodiment, the description and examples are intended to illustrate but not limit the scope of the invention, which is defined by the scope of the following claims.

We claim:

1. A method for the treatment of a patient who is suffering a stroke, said method comprising:
   identifying the stroke in an acute phase, said acute phase being defined as the first three hours from onset of the stroke; and
   applying continuous positive airway pressure to said patient at least during said acute phase of said stroke in order to improve the patient's blood oxygen level.

2. The method of claim 1 wherein said pressure is applied in a bi-level fashion.

3. The method of claim 1 wherein said patient's carbon dioxide blood level is reduced.

4. The method of claim 1 wherein auto regulation of blood pressure, cardiac output and ventilation is improved.

* * * * *